United States Patent [19]

Tukamoto et al.

[11] Patent Number: 4,536,601

[45] Date of Patent: Aug. 20, 1985

[54] OPTICALLY ACTIVE N-SUBSTITUTED PHENYLALANINOLS AND USE THEREOF

[75] Inventors: Masatoshi Tukamoto, Settsu; Tadahiro Sawayama, Kawanishi, both of Japan

[73] Assignee: Dainippon Pharmaceutical Co., Ltd., Osaka, Japan

[21] Appl. No.: 535,284

[22] Filed: Sep. 23, 1983

[30] Foreign Application Priority Data

Sep. 28, 1982 [JP] Japan .................. 57-172179
Sep. 28, 1982 [JP] Japan .................. 57-172180

[51] Int. Cl.$^3$ .................. C07C 91/02; C07D 317/44
[52] U.S. Cl. .................. 564/355; 549/443; 564/336; 564/373
[58] Field of Search .......... 564/336, 373, 355; 549/443

[56] References Cited

U.S. PATENT DOCUMENTS

| | | | |
|---|---|---|---|
| 3,804,899 | 4/1974 | Ebnother et al. | 549/443 |
| 4,224,457 | 9/1980 | Iwao et al. | 562/401 |
| 4,294,775 | 10/1981 | McKinnie | 562/401 X |
| 4,325,886 | 4/1982 | Ohashi et al. | 562/401 X |
| 4,372,969 | 2/1983 | Lafon | 549/443 |

FOREIGN PATENT DOCUMENTS

0008833  3/1980  European Pat. Off. .

OTHER PUBLICATIONS

Agr, Biol. Chem., 37(7) 1713–1716, 1973.
Chem. Abstr., 95 (1981), pp. 618, 6512b and ibid, pp. 624, 24281e.

*Primary Examiner*—Ethel G. Love
*Attorney, Agent, or Firm*—Wegner & Bretschneider

[57] ABSTRACT

Optically active N-substituted phenylalaninols of the formula (I):

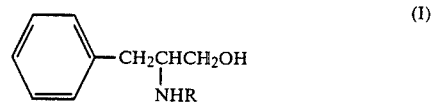

wherein R is isopropyl, 1-ethylpropyl, cyclopentyl, cyclohexyl, cycloheptyl, 4-methylbenzyl, 4-methoxybenzyl, or 3,4-methylenedioxybenzyl; and acid addition salts thereof which are useful as a resolving agent, and a process for preparing D-3-acetylthio-2-methylpropionic acid which comprises reacting DL-3-acetylthio-2-methylpropionic acid with an optically active N-substituted phenylalaninol of the formula (I) to form diastereomeric salts, subjecting the formed diastereomeric salts to a fractional crystallization from a solvent to separate the D-acid salt from the L-acid salt, and then decomposing the D-acid salt with a mineral acid to give D-3-acetylthio-2-methylpropionic acid.

3 Claims, No Drawings

OPTICALLY ACTIVE N-SUBSTITUTED PHENYLALANINOLS AND USE THEREOF

The present invention relates to novel optically active N-substituted phenylalaninols useful as a resolving agent and a process for preparing D-3-acetylthio-2-methylpropionic acid by the use of the N-substituted phenylalaninols as a resolving agent.

Organic acids which contain a chiral center are usually prepared by synthetic methods which result in a racemic form of the compound. Frequently, biological properties of such compounds are associated primarily, and in some cases exclusively, with one of the possible enantiomers and, therefore, it is desirable and often necessary to resolve the racemic mixture.

A frequently used method, among the known procedures for resolving a racemic mixture, employs the difference in properties between the diastereomeric salts obtained upon reaction of a racemic acid with an optically active amine. Such a procedure comprises mixing the racemic mixture with an optically active amine in an appropriate solvent, separating the resulting diastereomers, and decomposing the separated diastereomers to the optical isomers of the acid.

It is disclosed in Agr. Biol. Chem., 37, 1713–1716 (1973) that the resolution of (±)-trans-chrysanthemic acid with N-benzyl-L-phenylalaninol gave (−)-trans-chrysanthemic acid in a 31.7% yield.

D-3-Acetylthio-2-methylpropionic acid has a chemical structure of the formula:

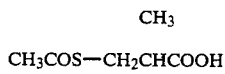

and is useful as a starting material for preparing 1-(D-3-mercapto-2-methylpropionyl)-L-proline (generic name: captopril) or 1-(D-3-acetylthio-2-methylpropionyl)-L-prolyl-L-phenylalanine (cf. U.S. Pat. No. 4,248,883), which are useful as antihypertensive agents.

It is known that D-3-acetylthio-2-methylpropionic acid is prepared by reacting a racemic mixture of said acid with cinchonidine, abietylamine derivatives, optically active 1,2-diphenylethylamine derivatives or 2-amino-1,1-diphenylpropanol to obtain the corresponding diastereomeric salts, subjecting the salts to a fractional crystallization from a suitable solvent, separating the resulting desired D-acid salt, and decomposing the D-acid salt (cf. U.S. Pat. No. 4,224,457, Japanese Patent Publication (unexamined) No. 118,455/1980 [Chem. Abstr., 95, 6512b (1981)], Japanese Patent Publication (unexamined) No. 7,756/1981 [Chem. Abstr., 95, 24281e (1981)], U.S. Pat. No. 4,325,886, and U.S. Pat. No. 4,294,775). Besides, European Patent Publication No. 0008833 discloses a method for preparing D-3-acetylthio-2-methylpropionic acid which comprises resolving the racemic mixture of 3-benzoylthio-2-methylpropionic acid with cinchonidine or D-(−)-2-aminobutanol as a resolving agent to obtain the corresponding D-acid, hydrolyzing the resulting D-acid to obtain D-3-mercapto-2-methylpropionic acid, and then acetylating the latter.

The present inventors have intensively studied an excellent resolving agent suitable for preparing D-3-acetylthio-2-methylpropionic acid. As a result, it has been found that certain optically active N-substituted phenylalaninols are particularly suitable as resolving agents for obtaining said acid.

An object of the present invention is to provide novel optically active N-substituted phenylalaninols and salts thereof useful as a resolving agent. Another object of the invention is to provide an excellent method for preparing D-3-acetylthio-2-methylpropionic acid by resolving the racemic mixture thereof using the optically active N-substituted phenylalaninols as a resolving agent. These and other objects and advantages of the present invention will be apparent to persons skilled in the art from the following description.

The optically active (L- or D-) N-substituted phenylalaninols of the present invention have a chemical structure of the formula:

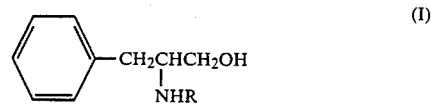

wherein R is isopropyl, 1-ethylpropyl, cyclopentyl, cyclohexyl, cycloheptyl, 4-methylbenzyl, 4-methoxybenzyl, or 3,4-methylenedioxybenzyl.

The compounds of the formula (I) can be prepared, for example, by reacting L- or D-phenylalaninol with a compound of the formula:

or

wherein $R_1$ is methyl or ethyl, or two $R_1$ groups combine to form tetramethylene, pentamethylene or hexamethylene; and $R_2$ is 4-methylphenyl, 4-methoxyphenyl, or 3,4-methylenedioxyphenyl, under reduction conditions.

The above reductive reaction is carried out, for example, by adding a reducing agent to a solution of L- or D-phenylalaninol and a compound of the formula (II) or (III) in an appropriate solvent, or by subjecting the solution to a catalytic reduction. The solvent includes alcohols such as methanol, ethanol, isopropyl alcohol; ethers such as tetrahydrofuran, dioxane; acetonitrile; dimethylformamide, or the like. The solvent used should properly be selected depending on the kinds of reducing agent or reducing means used. Suitable examples of the reducing agent are sodium borohydride, sodium cyanoborohydride, sodium bis(2-methoxyethoxy)aluminum hydride, diborane, lithium aluminum hydride, or the like. The catalytic reduction may usually be carried out under atmospheric pressure or under higher pressure by using, for example, platinum or Raney nickel as the catalyst. The above reaction is usually carried out at a temperature of from 0° to 50° C., optionally in the presence of a slight amount of glacial acetic acid.

The compound (I) can be isolated from the reaction mixture and purified by conventional methods. The compound (I) thus produced can be converted into the corresponding acid addition salt thereof by treating it with various inorganic acids (e.g. hydrochloric acid, hydrobromic acid, sulfuric acid, phosphoric acid) or various organic acids (e.g. oxalic acid, maleic acid, fumaric acid) in a usual manner.

The starting L- or D-phenylalaninol can be prepared from L- or D-phenylalanine lower alkyl ester by a known method, for example, as disclosed in Chem. Pharm. Bull., 13, 995 (1965).

The present invention provides also a process for preparing D-3-acetylthio-2-methylpropionic acid which comprises reacting DL-3-acetylthio-2-methylpropionic acid with an optically active N-substituted phenylalaninol of the formula (I) to form diastereomeric salts, subjecting the formed diastereomeric salts to a fractional crystallization from a solvent to separate the D-acid salt from the L-acid salt, and then decomposing the D-acid salt with a mineral acid to give D-3-acetylthio-2-methylpropionic acid.

The above process is carried out as follows. Firstly, DL-3-acetylthio-2-methylpropionic acid is reacted with an optically active N-substituted phenylalaninol of the formula (I) in an appropriate solvent to form diastereomeric salts. The N-substituted phenylalaninol (I) is usually used in an amount of 0.5 to 1.0 mole, preferably 0.6 to 0.85 mole, per 1 mole of DL-3-acetylthio-2-methylpropionic acid. Examples of the solvent are acetone, methyl ethyl ketone, methanol, ethanol, isopropyl alcohol, ethyl acetate, acetonitrile, hexane, toluene, dimethylformamide, or a mixture of these solvents, among which acetone or ethyl acetate is particularly suitable. This reaction is usually carried out by adding a solution of an optically active N-substituted phenylalaninol in a solvent to a solution of DL-3-acetylthio-2-methylpropionic acid in a solvent to form a uniform solution, or dissolving both compounds in a solvent with heating, preferably followed by adding a seed crystal of the desired diastereomeric salt.

In the above resolving step, when L-isomer of the N-substituted phenylalaninol (I) is used, there is preferentially precipitated a diastereomeric salt of D-3-acetylthio-2-methylpropionic acid whose solubility in the solvent is relatively small compared to that of a diastereomeric salt of the L-acid. The precipitated salt is separated by filtration and is optionally recrystallized from an appropriate solvent (e.g. ethyl acetate, acetone, ethanol, acetonitrile), and then, the salt is decomposed to give the desired D-3-acetylthio-2-methylpropionic acid.

When D-isomer of the N-substituted phenylalaninol (I) is used, a diastereomeric salt of L-3-acetylthio-2-methylpropionic acid is preferentially precipitated, and hence, after separating the precipitated salt by filtration, the mother liquor is concentrated, and the residue is dissolved in an aqueous solution of a mineral acid and extracted with ethyl acetate. To the ethyl acetate extract is added L-isomer of the N-substituted phenylalaninol (I), and the precipitated diastereomeric salt of D-3-acetylthio-2-methylpropionic acid is isolated and then decomposed to give the desired D-3-acetylthio-2-methylpropionic acid.

The decomposition of diastereomeric salts can be carried out in a usual manner. For instance, an aqueous solution of the diastereomeric salts are acidified with an aqueous solution of a mineral acid (e.g. hydrochloric acid, sulfuric acid, phosphoric acid) and then is extracted with an organic solvent such as ethyl acetate, diethyl ether, chloroform, or dichloromethane to give the desired D-3-acetylthio-2-methylpropionic acid. The N-substituted phenylalaninol used as the resolving agent can almost quantitatively be recovered from the portion insoluble in the organic solvent.

Thus, the compound (I) of the present invention can easily be prepared from readily available starting materials by a simple reaction and also can easily be recovered from the reaction mixture after the resolution reaction in a high yield and further shows excellent resolving effect, and hence, it is very useful as a resolving agent.

When the N-substituted phenylalaninols (I) of the present invention are used as a resolving agent for obtaining D-3-acetylthio-2-methylpropionic acid, it is preferably used in the form of L-isomer. For this purpose, particularly preferred compounds are the compounds of the formula (I) wherein R is isopropyl, 4-methylbenzyl, 4-methoxybenzyl, or 3,4-methylenedioxybenzyl, most preferably R is isopropyl.

The compounds (I) and their salts of the present invention are also useful as a reagent for asymmetric synthesis, or an intermediate for preparing various medicines and agricultural chemicals.

The present invention is illustrated by the following Examples but should not be construed to be limited thereto. In the Examples, unless specified otherwise, the optical rotation was measured under the conditions of a temperature of 24°–26° C., in ethanol at c=1.0. The identification of the compound was carried out by elementary analysis, mass spectrum, IR spectrum, NMR spectrum, etc. Besides, the solvent shown by parentheses after the melting point means a solvent for recrystallization.

Moreover, the optical purity in Examples 6 to 11 and Comparative Example is calculated on the basis of the specific rotation ($[\alpha]_D-45.7°$) of D-3-acetylthio-2-methylpropionic acid which was prepared by reacting DL-3-acetylthio-2-methylpropionic acid with cinchonidine, subjecting the obtained diastereomeric salts to repeated fractional crystallizations from ethyl acetate until the optical rotation had been unchanged by further crystallization, and decomposing the obtained D-acid salt with 1N hydrochloric acid.

EXAMPLE 1

Preparation of N-isopropyl-L-phenylalaninol:

(a) A solution of L-phenylalaninol (9.07 g) in ethanol (30 ml), acetone (7 ml) and glacial acetic acid (0.3 ml) was gently refluxed for 45 minutes. After cooling, sodium borohydride (2.5 g) was added in small portions with stirring. After the addition, the mixture was stirred for 30 minutes with ice-cooling and for 2 hours at room temperature and then concentrated under reduced pressure. The residue was acidified with dilute hydrochloric acid and then made alkaline with aqueous sodium hydroxide. The resulting mixture was extracted with chloroform. The extract was dried over sodium sulfate and concentrated under reduced pressure. The residue was dissolved in ethanol and 35% ethanolic hydrogen chloride (5.5 ml) was added. The precipitate formed was collected by filtration and recrystallized from ethanol to give N-isopropyl-L-phenylalaninol hydrochloride (11.7 g), mp 208°–210° C., $[\alpha]_D-3.3°$ (c=1.0, methanol).

(b) L-phenylalaninol (31.3 g) was dissolved in a mixture of acetone (23 ml) and ethanol (120 ml). The solution was shaken in an atmosphere of hydrogen in the presence of platinum oxide (0.1 g) until the calculated amount of hydrogen was absorbed. The catalyst was filtered off and the filtrate was concentrated to dryness under reduced pressure to give N-isopropyl-L-phenylalaninol (40 g), mp 65°–66° C., $[\alpha]_D-5.4°$.

EXAMPLE 2

The following compounds were prepared from L- or D-phenylalaninol and the corresponding ketone compounds in substantially the same manner as described in Example 1, (b), and when necessary, converted into an appropriate acid salt.

N-(1-Ethylpropyl)-L-phenylalaninol hydrogen oxalate, mp 126°–130° C. (isopropyl alcohol), $[\alpha]_D-13.0°$.

N-Cyclopentyl-L-phenylalaninol
 free base: mp 49°–52° C. (hexane), $[\alpha]_D-8.7°$.
 hydrochloride: mp 211°–213° C. (ethanol), $[\alpha]_D-16.3°$.

N-Cycloheptyl-L-phenylalaninol
 free base: mp 77°–80° C. (ligroin), $[\alpha]_D-15.8°$.
 hydrochloride: mp 157°–160° C. (isopropyl alcohol), $[\alpha]_D-19.4°$.

N-Isopropyl-D-phenylalaninol hydrochloride, mp 200°–205° C.

EXAMPLE 3

Preparation of N-cyclohexyl-L-phenylalaninol:
N-Cyclohexyl-L-phenylalaninol hydrochloride was prepared from L-phenylalaninol and cyclohexanone in substantially the same manner as described in Example 1, (a), mp 211°–213° C. (ethanol).

EXAMPLE 4

Preparation of N-(4-methylbenzyl)-L-phenylalaninol:
A solution of L-phenylalaninol (6.0 g) and 4-methylbenzaldehyde (5.3 g) in ethanol (40 ml) was stirred for 30 minutes at room temperature. Sodium borohydride (2.0 g) was added in small portions with stirring and ice-cooling, and then the mixture was stirred for 1.5 hours at room temperature. After removal of the ethanol by evaporation, the residue was acidified with dilute hydrochloric acid and then made alkaline with aqueous sodium hydroxide. The resulting mixture was extracted with chloroform. The extract was dried over sodium sulfate and the solvent was evaporated. The residue was recrystallized from ethanol to give N-(4-methylbenzyl)-L-phenylalaninol (8.9 g), mp 125°–127° C., $[\alpha]_D-6.7°$.

EXAMPLE 5

The following compounds were prepared from L-phenylalaninol and the corresponding aldehyde compounds in substantially the same manner as described in Example 4, and recrystallized from ethanol.

N-(4-Methoxybenzyl)-L-phenylalaninol, mp 89°–91° C., $[\alpha]_D-6.4°$.

N-(3,4-Methylenedioxybenzyl)-L-phenylalaninol, mp 127°–129° C, $[\alpha]_D-6.6°$.

EXAMPLE 6

Resolution of DL-3-acetylthio-2-methylpropionic acid with N-isopropyl-L-phenylalaninol:
To a solution of DL-3-acetylthio-2-methylpropionic acid (720 g, 4.44 moles) in ethyl acetate (2.9 liters) was added a solution of N-isopropyl-L-phenylalaninol (600 g, 3.11 moles) in ethyl acetate (4 liters), and the resulting solution was seeded with N-isopropyl-L-phenylalaninolium D-3-acetylthio-2-methylpropionate (100 mg). The solution was allowed to stand overnight in a refrigerator. The precipitate formed was collected by filtration to give the crude salt (484 g, $[\alpha]_D-28.1°$), which was recrystallized from ethyl acetate (3.3 liters) to afford N-isopropyl-L-phenylalaninolium D-3-acetylthio-2-methylpropionate (426 g; 54%), mp 103°–104° C., $[\alpha]_D-31.5°$ (optical purity 100%).

A solution of the above-obtained salt (426 g) in water (420 ml) was acidified with 10% sulfuric acid (1.1 liters) and then extracted with ethyl acetate (1 liter). The extract was dried over sodium sulfate and evaporated to give D-3-acetylthio-2-methylpropionic acid (190 g; 53%), $[\alpha]_D-45.7°$ (optical purity 100%).

EXAMPLE 7

Resolution of DL-3-acetylthio-2-methylpropionic acid with N-(3,4-methylenedioxybenzyl)-L-phenylalaninol:
N-(3,4-Methylenedioxybenzyl)-L-phenylalaninol (2.1 g, 7.4 mmoles) and DL-3-acetylthio-2-methylpropionic acid (1.4 g, 8.6 mmoles) were dissolved in ethyl acetate (25 ml) with heating. The solution was allowed to stand at room temperature for some time and then cooled for 3 hours in a refrigerator. The precipitate formed was collected by filtration to afford the crude salt (2.5 g, $[\alpha]_D-16.2°$), which was twice recrystallized from ethyl acetate (each about 14 ml) to give N-(3,4-methylenedioxybenzyl)-L-phenylalaninolium D-3-acetylthio-2-methylpropionate (1.3 g), mp 98°–101° C.

A solution of the above-obtained salt (1.3 g) in water was acidified with 10% sulfuric acid and then extracted with ethyl acetate. The extract was dried over sodium sulfate and evaporated to give D-3-acetylthio-2-methylpropionic acid (0.46 g; 66%), $[\alpha]_D-36.7°$ (optical purity 80.3%).

EXAMPLE 8

Resolution of DL-3-acetylthio-2-methylpropionic acid with N-(4-methoxybenzyl)-L-phenylalaninol:
N-(4-Methoxylbenzyl)-L-phenylalaninol (2.0 g, 7.4 mmoles) and DL-3-acetylthio-2-methylpropionic acid (1.4 g, 8.6 mmoles) were dissolved in ethyl acetate (25 ml) with heating. The solution was slowly cooled to 5° C. and kept at this temperature for several hours. The precipitate formed was collected by filtration to afford the crude salt (1.8 g). Recrystallization from ethyl acetate (13 ml) gave N-(4-methoxybenzyl)-L-phenylalaninolium D-3-acetylthio-2-methylpropionate (1.0 g), mp 85°–87° C.

A solution of the above-obtained salt (1.0 g) in water was acidified with 10% sulfuric acid and then extracted with ethyl acetate. The extract was dried over sodium sulfate and evaporated to give D-3-acetylthio-2-methylpropionic acid (0.36 g; 51%), $[\alpha]_D-36.6°$ (optical purity 80.0%).

EXAMPLE 9

Resolution of DL-3-acetylthio-2-methylpropionic acid with N-(4-methylbenzyl)-L-phenylalaninol:
N-(4-Methylbenzyl)-L-phenylalaninol (1.9 g, 7.5 mmoles) and DL-3-acetylthio-2-methylpropionic acid (1.4 g, 8.6 mmoles) were dissolved in ethyl acetate (25 ml) with heating. The solution was slowly cooled to 5° C. and kept at this temperature for several hours. The precipitate formed was collected by filtration to afford the crude salt (2.1 g). Recrystallization from ethyl acetate (15 ml) gave N-(4-methylbenzyl)-L-phenylalaninolium D-3-acetylthio-2-methylpropionate (1.7 g), mp 107°–111° C.

A solution of the above-obtained salt (1.7 g) in water was acidified with 10% sulfuric acid and then extracted with ethyl acetate. The extract was dried over sodium sulfate and evaporated to give D-3-acetylthio-2-methylpropionic acid (0.64 g; 91%), [α]$_D$ −33.5° (optical purity 73.3%).

EXAMPLE 10

Resolution of DL-3-acetylthio-2-methylpropionic acid with N-isopropyl-L-phenylalaninol:

N-Isopropyl-L-phenylalaninol (1.9 g, 9.8 mmoles) and DL-3-acetylthio-2-methylpropionic acid (2.2 g, 13.6 mmoles) were dissolved in acetone (20 ml) with heating. The solution was slowly cooled to 5° C. and kept at this temperature for several hours. The precipitate formed was collected by filtration to give N-isopropyl-L-phenylalaninolium D-3-acetylthio-2-methylpropionate (1.3 g), mp 101°–102° C.

A solution of the above-obtained salt (1.3 g) in water was acidified with 10% sulfuric acid and then extracted with ethyl acetate. The extract was dried over sodium sulfate and evaporated to give D-3-acetylthio-2-methylpropionic acid (0.58 g; 53%), [α]$_D$ −40.8° (optical purity 89.3%).

EXAMPLE 11

Resolution of DL-3-acetylthio-2-methylpropionic acid with N-isopropyl-D-phenylalaninol:

N-Isopropyl-D-phenylalaninol (1.9 g, 9.8 mmoles) and DL-3-acetylthio-2-methylpropionic acid (2.7 g, 16.7 mmoles) were dissolved in ethyl acetate (22 ml) with heating. The solution was slowly cooled to 5° C. and kept at this temperature for several hours. The precipitate formed was collected by filtration to give N-isopropyl-D-phenylalaninolium D-3-acetylthio-2-methylpropionate (1.4 g, mp 101°–102° C., [α]$_D$ +27.8°). The filtrate was washed with 3% sulfuric acid and water, dried over sodium sulfate, concentrated to half of its original volume, and N-isopropyl-L-phenylalaninol (2.1 g) was added. The solution was allowed to stand overnight in a refrigerator. The precipitate formed was collected by filtration to give N-isopropyl-L-phenylalaninolium D-3-acetylthio-2-methylpropionate (2.2 g).

A solution of the above-obtained salt (2.2 g) in water was acidified with 10% sulfuric acid and then extracted with ethyl acetate. The extract was dried over sodium sulfate and evaporated to give D-3-acetylthio-2-methylpropionic acid (0.98 g; 73%), [α]$_D$ −43.9° (optical purity 96.1%).

EXAMPLE 12

The following diastereomeric salts were prepared from DL-3-acetylthio-2-methylpropionic acid and 0.6 equivalents of the corresponding N-substituted-L-phenylalaninols in substantially the same manner as described in Examples 8 and 9.

N-Cyclopentyl-L-phenylalaninolium D-3-acetylthio-2-methylpropionate, [α]$_D$ −18.0°

N-Cyclohexyl-L-phenylalaninolium D-3-acetylthio-2-methylpropionate, [α]$_D$ −20.3°

N-Cycloheptyl-L-phenylalaninolium D-3-acetylthio-2-methylpropionate, [α]$_D$ −20.0°

N-(1-Ethylpropyl)-L-phenylalaninolium D-3-acetylthio-2-methylpropionate, [α]$_D$ −23.1°

COMPARATIVE EXAMPLE

Resolution of DL-3-acetylthio-2-methylpropionic acid with N-benzyl-L-phenylalaninol:

N-Benzyl-L-phenylalaninol (1.8 g, 7.5 mmoles) and DL-3-acetylthio-2-methylpropionic acid (1.4 g, 8.6 mmoles) were dissolved in ethyl acetate (24 ml) with heating. The solution was allowed to stand at room temperature for some time and then cooled for 3 hours in a refrigerator. The precipitate formed was collected by filtration to afford the crude salt (1.2 g), which was recrystallized from ethyl acetate (9 ml) to give N-benzyl-L-phenylalaninolium D-3-acetylthio-2-methylpropionate (0.82 g).

A solution of the above-obtained salt (0.82 g) in water was acidified with 10% sulfuric acid and then extracted with ethyl acetate. The extract was dried over sodium sulfate and evaporated to give D-3-acetylthio-2-methylpropionic acid (0.31 g; 44%), [α]$_D$ −28.3° (optical purity 61.9%).

The optical purity and yield of D-3-acetylthio-2-methylpropionic acid obtained above are shown in Table 1 together with the results of Examples 7, 8 and 9, in which the N-substituted-L-phenylalaninols similar to N-benzyl-L-phenylalaninol in chemical structure were used as a resolving agent.

As is obvious from Table 1, the compounds of the present invention are far superior to N-benzyl-L-phenylalaninol as a resolving agent for DL-3-acetylthio-2-methylpropionic acid.

TABLE 1

| | Resolving Agent | Optical Purity (%) | Yield (%) | Yield × O.P. / 100 |
|---|---|---|---|---|
| Example 7 | N—(3,4-Methylenedioxybenzyl)-L-Pheol | 80.3 | 66 | 53.0 |
| Example 8 | N—(4-Methoxybenzyl)-L-Pheol | 80.0 | 51 | 40.8 |
| Example 9 | N—(4-Methylbenzyl)-L-Pheol | 73.3 | 91 | 66.7 |
| Comparative Example | N—Benzyl-L-Pheol | 61.9 | 44 | 27.2 |

The abbreviations used are as follows: Pheol, phenylalaninol; O.P., Optical Purity.

What is claimed is:

1. An optically active N-substituted phenylalaninol of the formula:

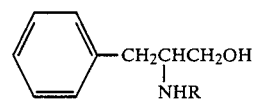

wherein R is isopropyl, 1-ethylpropyl, cyclopentyl, cyclohexyl, cycloheptyl, 4-methylbenzyl, 4-methoxybenzyl, or 3,4-methylenedioxybenzyl, or an acid addition salt thereof.

2. The optically active N-substituted phenylalaninol of claim 1 wherein R is isopropyl.

3. The optically active N-substituted phenylalaninol of claim 1 wherein R is 4-methylbenzyl, 4-methoxybenzyl or 3,4-methylenedioxybenzyl.

* * * * *